United States Patent
Fang et al.

(10) Patent No.: US 7,158,663 B2
(45) Date of Patent: Jan. 2, 2007

(54) METHOD FOR MEASURING CONFIDENCE OF BALL GRID ARRAY MODEL IN SURFACE MOUNTED DEVICES

(75) Inventors: Tong Fang, Morganville, NJ (US); Ming Fang, Princeton Jct., NJ (US)

(73) Assignee: Siemens Corporate Research, Inc., Princeton, NJ (US)

( * ) Notice: Subject to any disclaimer, the term of this patent is extended or adjusted under 35 U.S.C. 154(b) by 833 days.

(21) Appl. No.: 10/420,286

(22) Filed: Apr. 22, 2003

(65) Prior Publication Data

US 2004/0213451 A1 Oct. 28, 2004

(51) Int. Cl.
*G06K 9/00* (2006.01)

(52) U.S. Cl. .......................... 382/145; 29/833; 438/16

(58) Field of Classification Search ................ 382/100, 382/144, 145, 146; 29/833; 438/16
See application file for complete search history.

(56) References Cited

U.S. PATENT DOCUMENTS 5,736,790 A * 4/1998 Iyogi et al. ................ 257/780
6,177,682 B1 * 1/2001 Bartulovic et al. ..... 250/559.44
6,496,270 B1 * 12/2002 Kelley et al. ............... 356/602
2004/0126005 A1 * 7/2004 Duvdevani et al. ......... 382/149

* cited by examiner

Primary Examiner—Vikkram Bali
Assistant Examiner—Anand Bhatnagar
(74) Attorney, Agent, or Firm—Donald B. Paschburg; F.Chau & Associates, LLC

(57) ABSTRACT

A method for obtaining confidence measure of a ball grid array (BGA) model having a plurality of balls in semiconductor surface mounted devices is provided. The method comprises the steps of extracting BGA images from a real surface mounted device, generating a BGA ball model and a BGA body model, generating a first confidence measure of the BGA ball model wherein the first confidence measure includes a first standard deviation of the BGA ball model and a first local image contrast of each BGA ball, and generating a second confidence measure of the BGA body model wherein the second confidence measure includes a second standard deviation of the BGA body model and a second local image contrast of the BGA body.

30 Claims, 12 Drawing Sheets

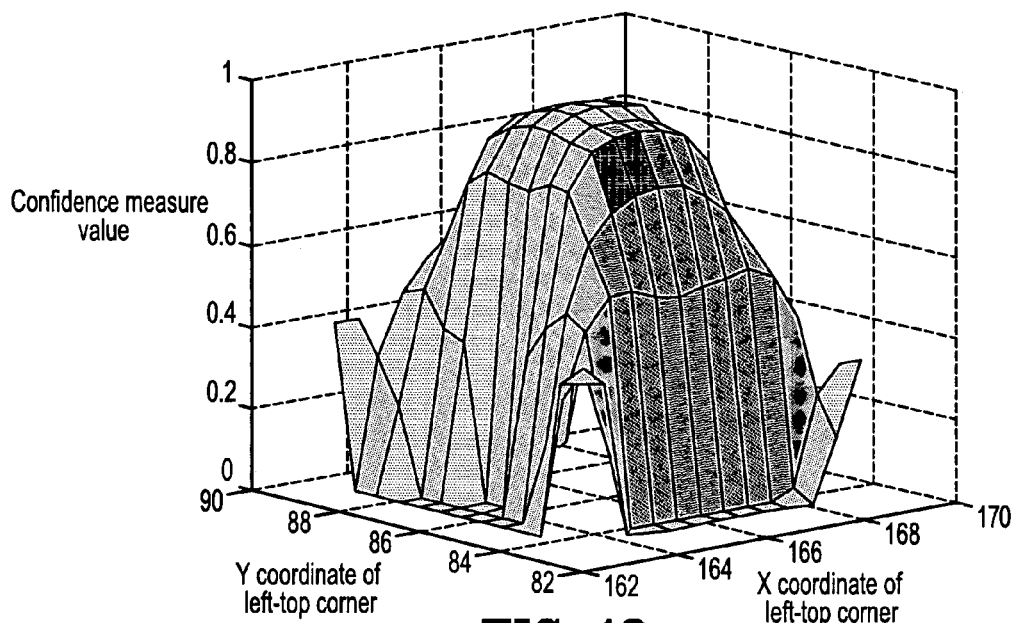
FIG. 12a
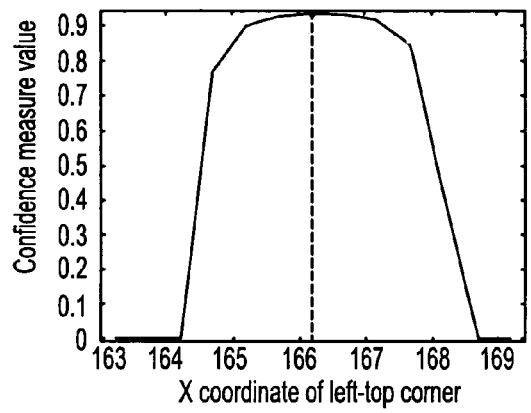 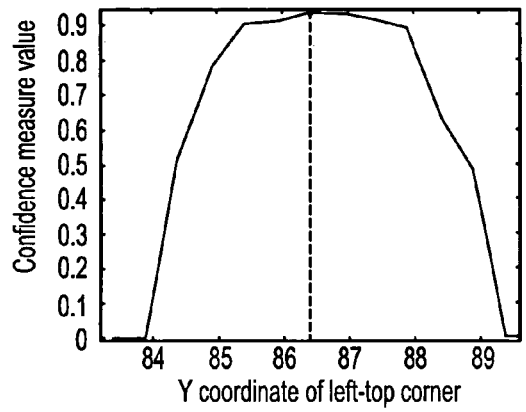
FIG. 12b          FIG. 12c
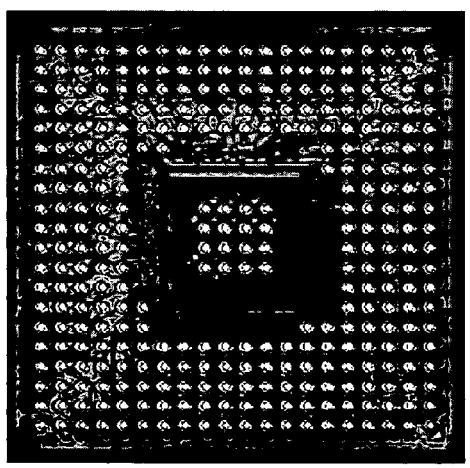 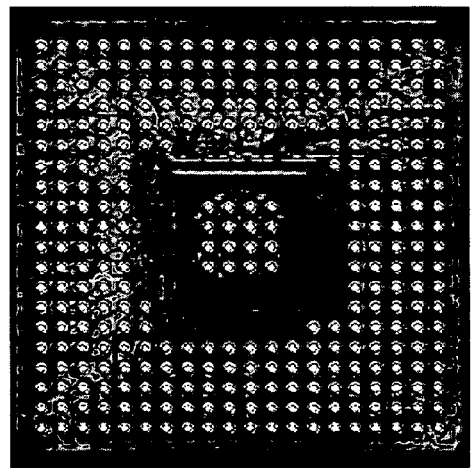
FIG. 12d          FIG. 12e

METHOD FOR MEASURING CONFIDENCE OF BALL GRID ARRAY MODEL IN SURFACE MOUNTED DEVICES

BACKGROUND

1. Field of the Invention

The present invention relates to a method for modeling a ball grid array (BGA) of surface mounted devices and, more particularly, to a method for measuring confidence of a BGA model in semiconductor surface mounted devices.

2. Discussion of Related Art

In chip packaging technology, 'Ball Grid Array' (BGA) has been used, particularly, in semiconductor Surface Mounted Devices (SMD). With BGA, more electrical connections between chips and printed circuit boards can be made because the electrical connections are on the underside of the chip, freeing up more space than the conventional chips having surround edge connections.

There are many ways to inspect the semiconductor Surface Mounted Devices. Among them, inspection by illumination inspection, a low-power lens or stereo microscope and an automated x-ray inspection system are the most common.

A disadvantage of BGA packaging is that visual inspections are difficult because, once the chip is attached to the circuit board, the electrical connections are hidden under the package. Thus, model based techniques are being used and are continually being developed to improve on inspection applications in semiconductor Surface Mounted Devices. The SMD component model in general contains information about the geometric structures and properties of the SMD component. The main advantages of the model based technique for inspection of SMD components are easy adaptability of a SMD model to different imaging sensor parameters, easy modification of the model, and editing capability.

A SMD component model can be generated either from a CAD data file describing the SMD component or from images of the actual SMD component to be tested or inspected. When the CAD data file is not available, the SMD component model is generated using images that are extracted from the SMD component. Typically, one to two images of an actual SMD component are used for modeling the device through image extraction techniques.

Because no geometric description about the SMD component is available before the model generation process, it is difficult to measure the correctness of the modeling results directly by comparing the extracted model to the real component. Therefore, a need exists for modeling precisely the SMD component and obtaining accurate measurements with high level of confidence of the correctness of the model.

SUMMARY OF THE INVENTION

The present invention is directed to a method for obtaining confidence measure of a ball grid array (BGA) model having a plurality of balls and a body in semiconductor surface mounted devices. According to an embodiment of the present invention, the method comprises the steps of extracting BGA images from a real surface mounted device, generating a BGA ball model and a BGA body model, generating a first confidence measure of the BGA ball model wherein the first confidence measure includes a first standard deviation of the BGA ball model and a first local image contrast of each BGA ball, and generating a second confidence measure of the BGA body model wherein the second confidence measure includes a second standard deviation of the BGA body model and a second local image contrast of the BGA body.

To generate the first confidence measure, a local ball window having a plurality of pixels is selected and the size of the local window is set to be greater than or equal to a diameter of a ball of the plurality of pixels such that the local window completely encompasses the ball. Then, the local ball window is placed symmetrically around the ball such that a window center corresponds to a ball center. The first standard deviation is calculated as a function of an image vector of the ball window containing a specific ball, a mean vector of a number of BGA ball windows, and a length of the image vector. Here, the mean vector of the number of BGA ball windows is calculated by dividing a sum of all image vectors by the number of all BGA ball windows.

The first local image contrast is calculated using a gradient operation based on a magnitude of an image gradient vector along a direction that is perpendicular to the tangent of the ball model.

The step of generating the first confidence measure further comprises the step of obtaining four local image contrast values of the BGA ball model to thereby calculate a local image contrast value of each ball of the BGA ball model. Each of the four local image contrast values is calculated as a function of a plurality of magnitudes of image gradient vectors along different directions that are perpendicular to the tangent of the ball model at the left, the right, the top, or the bottom side of the ball model, respectively. The first local image contrast of the BGA ball model having a number of BGA balls is generated using the obtained four local image contrast values. Then, the confidence measure for the BGA ball model is obtained by a function of the first standard deviation of the BGA ball model and the first local image contrast.

According to another embodiment of the present invention, the step of generating a second confidence measure of the BGA body model comprises selecting a local window encompassing a boundary line of a plurality of body boundary lines that define the BGA body. The local window contains a number of pixels having a line length and a predefined size of the local window perpendicular to a specific line direction. The step of generating the second confidence measure further comprises dividing the local window into a number of segments to obtain mean value of the number of segments of the boundary line. Then, standard deviation of the boundary line is calculated using an obtained mean value of the plurality of segments. Next, mean standard deviation of the BGA body model having a number of boundary lines is calculated.

The step of generating the second confidence measure of the BGA body model further comprises calculating the local image contrast of the BGA body model. Typically, the step of calculating the local image contrast is performed for each segment of the boundary line by a gradient operation. To calculate the local image contrast of the BGA body model, each boundary line is selected in turn among a plurality of boundary lines that form the BGA body model. A line local image contrast for each boundary line is obtained using a function including a parameter of a magnitude of an image gradient vector for each segment. Then, the method proceeds to obtaining the second local image contrast value of the BGA body having a number of boundary lines. Accordingly, the confidence measure for the BGA body model is generated using parameters of the second standard deviation and the second local image contrast value of the BGA body.

BRIEF DESCRIPTION OF THE DRAWINGS

A more complete appreciation of the invention, and many of the attendant advantages thereof, will be readily apparent with reference to the following detailed description when considered in conjunction with the accompanying drawings in which like reference symbols indicate the same or the similar components, wherein:

FIGS. 12(a) through 12(e) show confidence measure values and image examples based on incorrect x or y position of the top-left corner ball with consequently low confidence measure;

DETAILED DESCRIPTION OF PREFERRED EMBODIMENTS

Preferred embodiments of the present invention will now be described hereinafter with reference to the accompanying drawings. The present invention may, however, be embodied in many different forms and should not be construed as limited to the embodiments set forth herein.

It is to be understood that the systems and methods described herein in accordance with the present invention may be implemented in various forms of hardware, software, firmware, special purpose processors, or a combination thereof. Preferably, the present invention is implemented in software as an application comprising program instructions that are tangibly embodied on one or more program storage devices (e.g., magnetic floppy disk, RAM, CD Rom, ROM and flash memory), and executable by any device or machine comprising suitable architecture.

It is to be further understood that since the constituent system modules and method steps depicted in the accompanying Figures are preferably implemented in software, the actual connection between the system components (or the flow of the process steps) may differ depending upon the manner in which the present invention is programmed. Given the teachings herein, one of ordinary skill in the related art will be able to contemplate these and similar implementations or configurations of the present invention.

Figure 1:
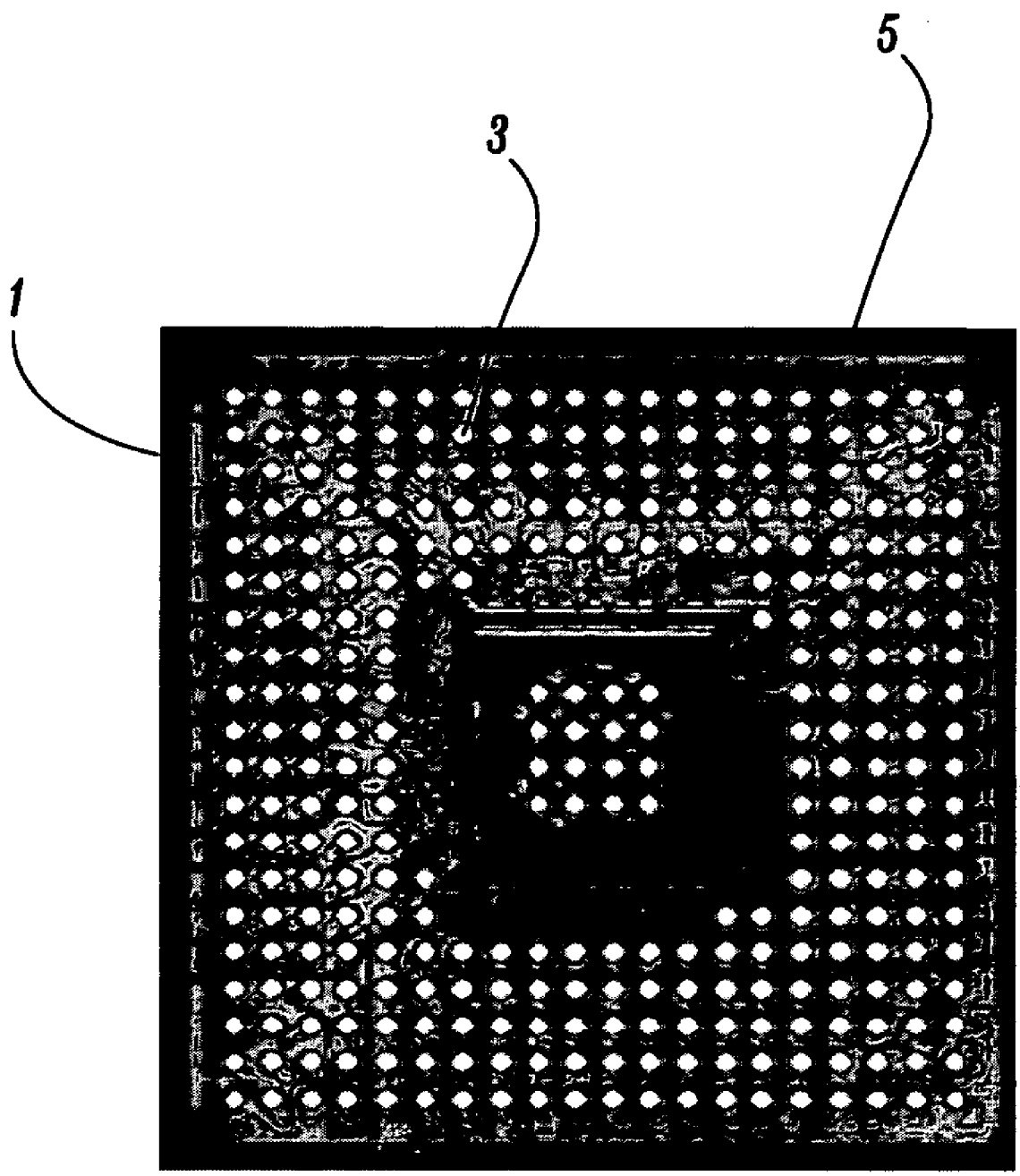
FIG. 1 is an image of a typical BGA component that contains a plurality of balls and a body.

FIG. 1 shows an image of a typical BGA component 1 that contains a plurality of balls 3 and a body 5 having a plurality of boundary lines at the left, right, top, and bottom side. All BGA balls in the BGA component are in general located within a BGA body boundary on a regular grid as shown in FIG. 1. To describe the BGA component completely, the model at least contains geometric information of all BGA balls and the BGA body, including position, diameter, the inter-ball distance of all balls, and a total number of balls as well as body's size, orientation, and location. Because of the very distinct nature of BGA balls and the body boundary, BGA modeling can be divided into following two parts: BGA ball modeling and BGA body modeling.

The geometric shape of a SMD component usually consists of circles and lines. A SMD component model can be built by extracting the geometric information of those lines and/or circles. Therefore, the confidence measure for the SMD component model can essentially be achieved by determining the confidence measure of the lines and circles in the SMD component model.

The confidence measure of the lines and circles in the SMD model can mainly be determined by two following factors: the modeling accuracy, which is related to the consistency of the model, and the image quality, which is typically realized by image contrast. High modeling accuracy and high image quality lead to high confidence measure of the modeling process. A model standard deviation in the image domain is proposed as an indicator for the modeling accuracy and the local image contrast along the model lines and circles as an indicator for image quality. The main reason for selecting the local image contrast as an indicator for image quality is the fact that most images for SMD model generation are taken under different illumination conditions optimized for different parts of a SMD component. For example, one illumination may lead to the perfect imaging of balls and the other may be perfect for the body imaging. Since the main effect of different illuminations is conspicuously reflected in the changing image contrast for different part of the SMD component, the local image contrast is a good and sensible indicator about how well or easily the localization of balls and lines of the body can be performed.

Preferably, other local statistical measures may also be added. Because high local image contrast and low model variation in the image domain indicate a high confidence of the modeling process, a combined confidence measure of the modeling process is defined as follows based on both factors:

$$p = 1 - k\frac{\sigma}{\delta}, \tag{1}$$

where $\sigma$ is the standard deviation of the obtained model in the image domain; $\delta$ is the local image contrast along lines and circles; and $k$ is a constant, which is used to map the ratio of $\sigma/\delta$ into the interval of $[0, 1]$.

Figure 2:
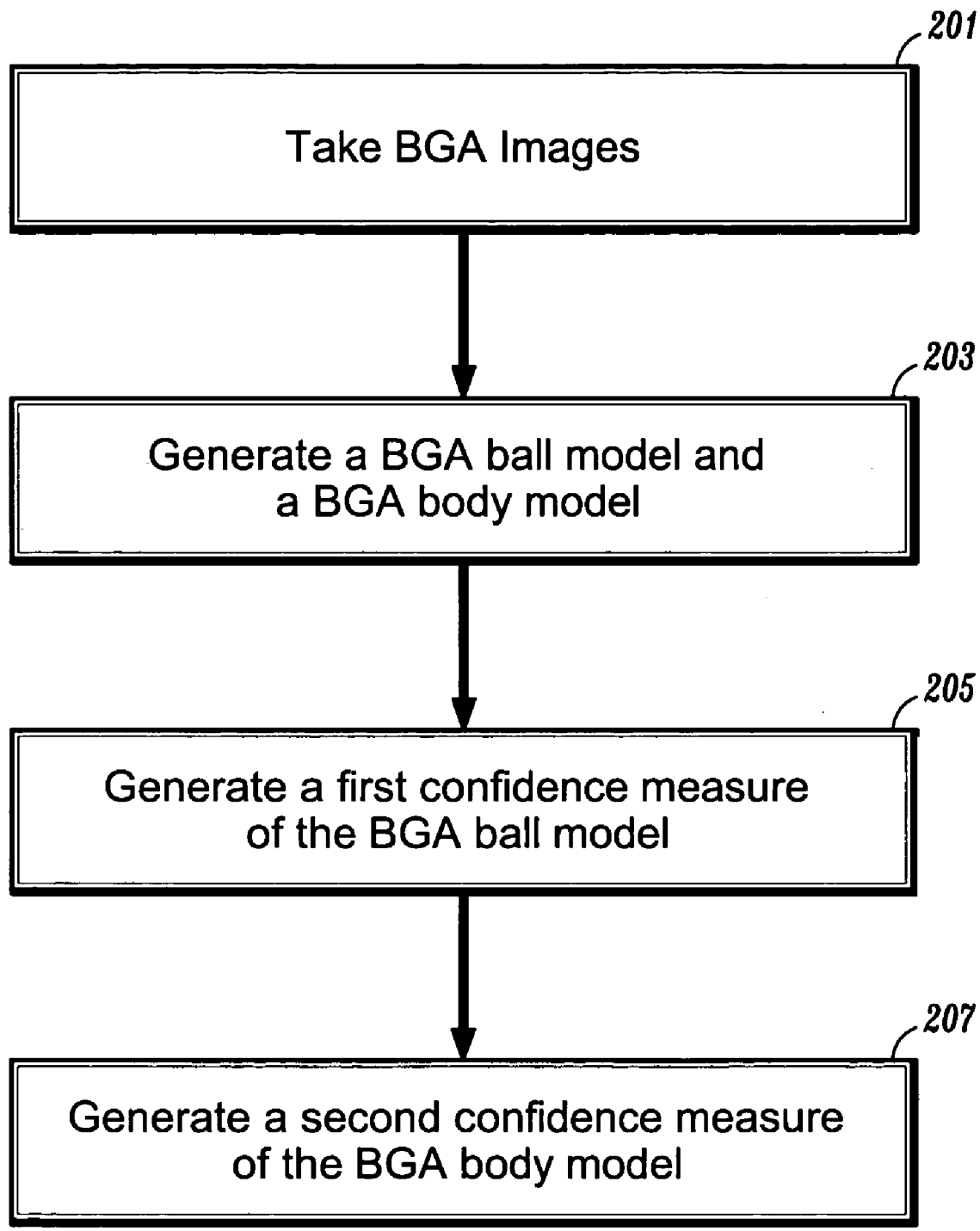
FIG. 2 illustrates an overall process of generating confidence measures of a BGA ball and a BGA body according to an embodiment of the present invention.

FIG. 2 illustrates an overall process of generating confidence measures of a BGA ball and a BGA body according to an embodiment of the present invention. An SMD component model can be generated either from a CAD data file describing an SMD component or from one to two images of the SMD component. As shown in step 201, the SMD component model is generated from images. Typically, images of the SMD component is directly extracted from the real SMD component through some image processing and extraction techniques. In step 203, a BGA ball model and a BGA body model are generated. Next, a first confidence measure of a BGA ball model is generated in step 205, wherein the first confidence measure includes a first standard deviation of the BGA ball model and a first local image contrast of each BGA ball. In step 207, a second confidence measure of a BGA body model is generated wherein the second confidence measure includes a second standard deviation of the BGA body model and a second local image contrast of the BGA body. Each step of 203, 205, and 207 will be described in more detail associated with FIGS. 3 and 5.

Figure 3:
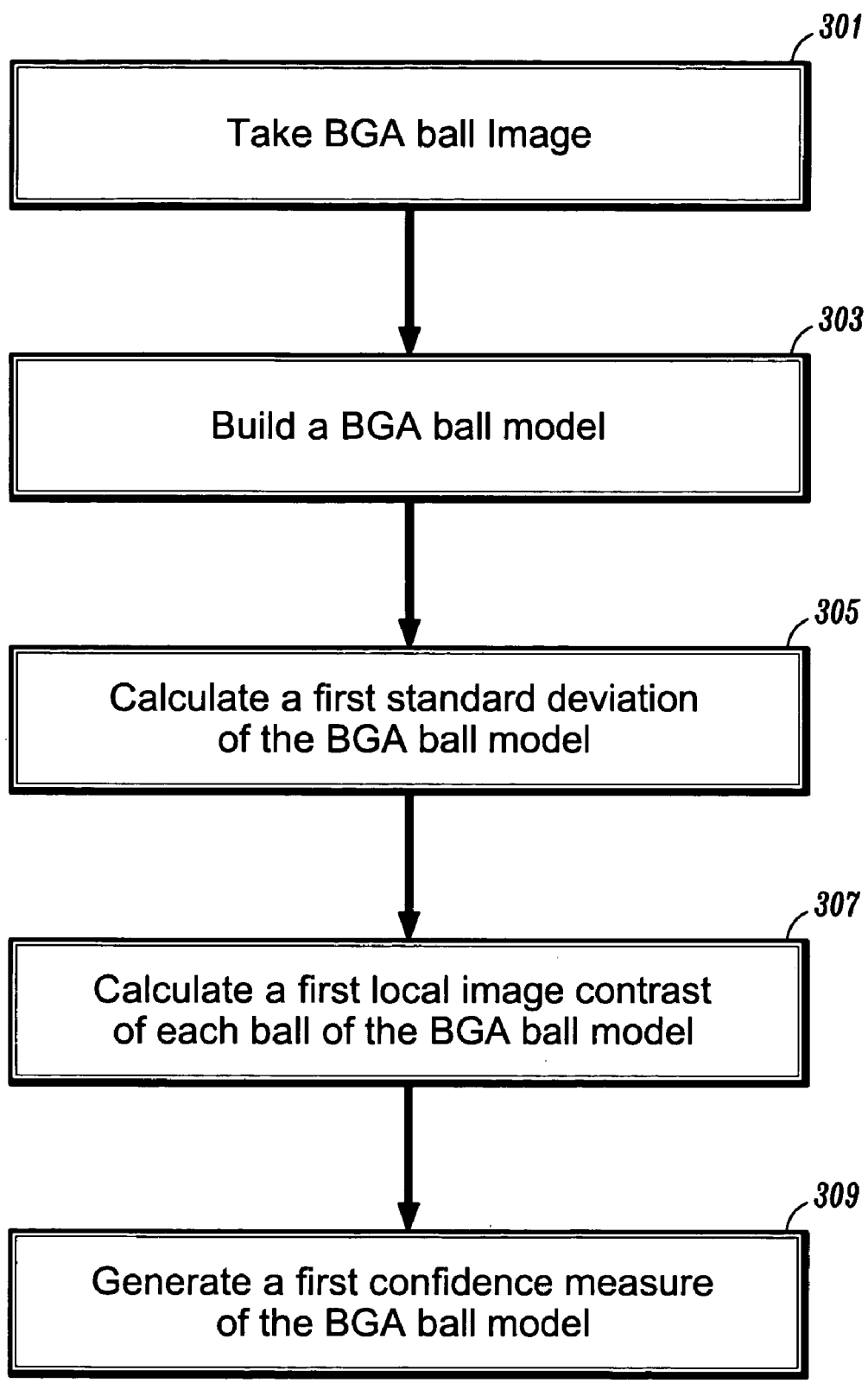
FIG. 3 illustrates a detailed process of generating a first confidence measure of a BGA ball model according to an embodiment of the present invention.

FIG. 3 illustrates a process of generating a first confidence measure of a BGA ball according to an embodiment of the present invention. As an initial step to the generation of a first confidence measure of the BGA ball model, one or two images of the SMD component is directly extracted from the real SMD component through image processing and extraction techniques in step 301.

In step 303, the BGA ball model is achieved by setting a plurality of regions of interest (ROIs) for all BGA balls to be modeled through a BGA ball detection process, and building a grid model that includes a grid orientation, a grid horizontal displacement, a grid vertical displacement, the maximum number of balls in a row/column, and a coordinate of a top-left corner ball center. If at least one ball is detected inside of ROIs, BGA ball information is extracted by calculating a ball center coordinate and a diameter of each detected ball.

Then, this method proceeds to building a BGA ball model that contains geographic information of the BGA balls. The building step comprises determining a grid horizontal displacement and a grid vertical displacement. The grid horizontal displacement is determined based on the maximum frequency of the minimum horizontal distance histogram by using the minimum horizontal distance of each ball located inside the maximum bin of the histogram and the total number of balls located in the maximum frequency bin of the histogram. Likewise, the grid vertical displacement is determined based on the maximum frequency of the minimum vertical distance histogram by using the minimum vertical distance of each ball located inside the maximum bin of the histogram and the total number of balls located in the maximum frequency bin of the histogram. Preferably, the BGA ball orientation is obtained based on a ball horizontal angle and a ball vertical angle.

A BGA top-left corner coordinate is determined which is defined as the intersection of a first row gird line and a first column grid line, wherein the first row grid line is generated by connecting the centers of the first ball and the last ball in the first row, the first column grid line being generated by connecting the centers of the first ball and the last ball in the first column.

Preferably, the modeling of the ball grid array further comprises fine-tuning the parameters that are calculated in the previous step. The fine-tuning includes the step of fine-tuning a horizontal inter-ball distance and a vertical inter-ball distance by averaging inter-ball distances of all rows/columns to further tune BGA model parameters, the step of fine-tuning a BGA ball orientation by averaging each horizontal angle and each vertical angle, wherein the first and last balls in each row/column are used to have the longest distance, and the step of fine-tuning the BGA top-left corner coordinate by using local and global BGA ball contrast calculation. All BGA balls are localized by verifying whether there is a ball on the grid intersection and the modeling of the grid array is completed by combining the information of the grid model and the information of BGA ball positions and diameters. Preferably, verifying is performed using dominant circle detection process.

In step 305, a first standard deviation of the BGA ball model is calculated to generate the first confidence measure. Step 305 will be explained more fully in association with FIG. 4.

Figure 4:
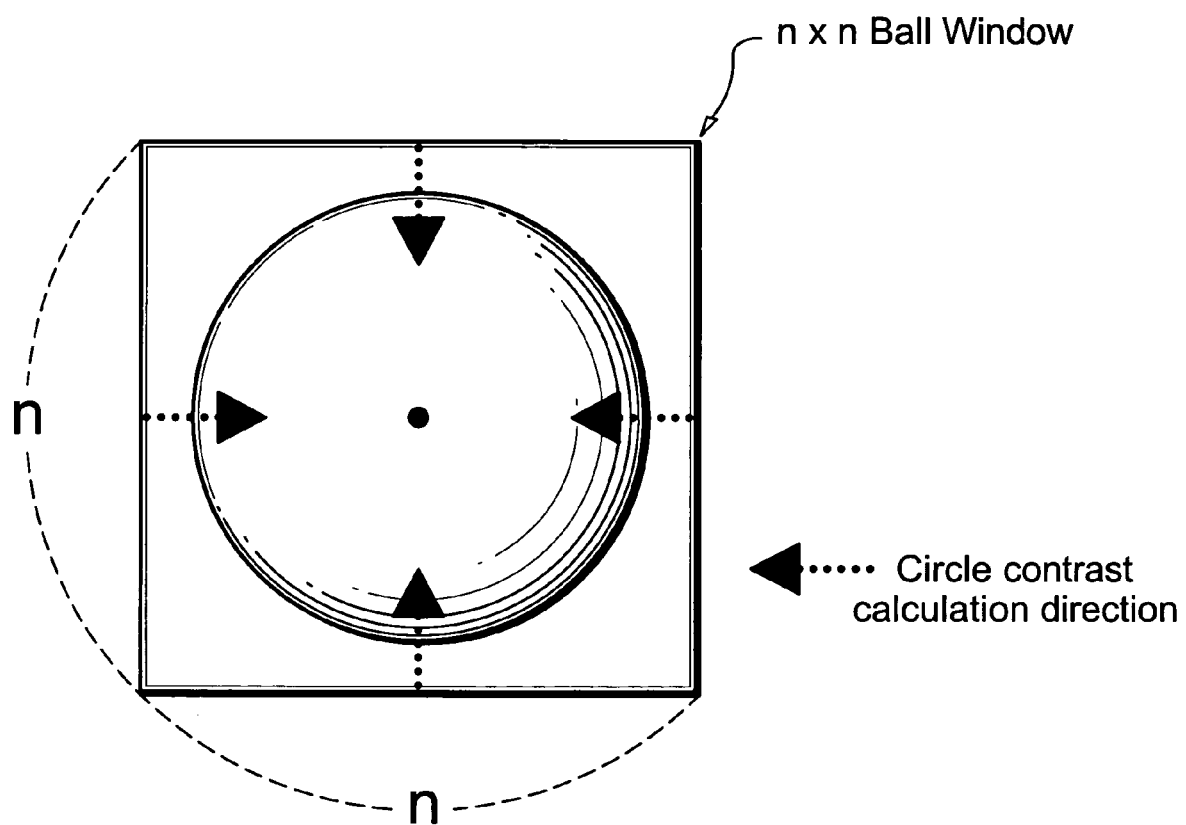
FIG. 4 shows a n×n ball window encompassing a ball of a BGA ball model.

FIG. 4 shows a n×n ball window encompassing a ball of a BGA ball model where n is the number of pixels. Although confidence measure calculation for different circle modeling applications may not exactly be the same, the basic idea is similar. It is assumed that a BGA component image contains only one BGA component, all BGA balls of one BGA component are identical and visible, and the illumination condition is the same for all balls.

The local ball window with n by n pixels is selected and the size of the local window is set to be greater than or equal to a diameter of a ball such that the local window completely encompasses the ball. Then, the local ball window is placed symmetrically around the ball such that a window center corresponds to a ball center.

Under the above assumptions, if the BGA ball model containing information about ball centers, average ball diameter, and inter-ball distance in both horizontal and vertical directions, is correctly and accurately generated, then all of the so-called ball windows as shown in FIG. 4 containing each ball extracted from the BGA component image according the BGA model should be identical, and the standard deviation of these ball windows should results in being small. However, if the BGA model is not accurate in describing the ball center positions, the ball windows containing each ball will have somewhat varying image content that leads to an increased standard deviation of these ball windows. In addition, if a non-ball structure is falsely identified as a ball or if the inter-ball distance is not accurately modeled, it also leads to greater standard deviation of these ball windows. Therefore, the standard deviation of these ball windows is one of good factors measuring and indicating how accurate the ball positions are determined and whether some foreign structures are falsely identified as balls.

For given the image containing the BGA component 1 in FIG. 1, a set of N BGA balls are first localized during the BGA ball modeling process, where N is the total number of balls to be modeled. For every BGA ball, a local window with n by n pixels, which encompasses the ball completely, is then selected from the BGA component image. The local window size 'n' is selected to be greater than or equal to the ball's diameter, as shown in FIG. 4. The local ball window is placed symmetrically around the ball so that the window center corresponds to the ball center. Let $X_i$ be an image vector of the ball window containing the i-th ball. The length 'L' of the vector $X_i$ is equal to $n^2$.

The mean vector $\overline{X}$ of N BGA ball windows can be calculated as $$\overline{X} = \frac{\sum_{i=1}^{N} X_i}{N}. \tag{2}$$

And then the model standard deviation of the BGA ball in the image domain is obtained as follows:

$$\sigma = \frac{\sum_{j=1}^{L}\left(\sqrt{\frac{\sum_{i=1}^{N}(X_i-\overline{X})^2}{N-1}}\right)}{L}. \quad (3)$$

As described above, combined confidence measure actually consists of the following two parts: the model standard deviation in the image domain and the local image contrast along the modeled areas.

Continuously associated with FIGS. 3 and 4, the step 307 for local Image contrast calculation of BGA balls will be discussed in the context of BGA ball modeling. The local image contrast of a BGA ball is obtained from the local image contrast around the circle edge area. Since high local image contrast around the circle edge area in general means easier and more accurate circle edge localization, it leads to high confidence in the ball modeling process. The contrast of each ball is calculated by a gradient operation along the direction that is perpendicular to the circle tangent:

$$\Delta = \max|A(k)-A(k-1)| \quad (4).$$

For simplicity, only gradient operations along the horizontal and the vertical direction are considered, as shown by the four arrows in FIG. 4. In total, four local image contrast values of a circle, called the left, right, top and bottom contrast, can be obtained. The final local image contrast value of the i-th ball can be calculated by $$\delta_i = \frac{\Delta_{left}+\Delta_{right}+\Delta_{top}+\Delta_{bottom}}{4}. \quad (5)$$

Then, the local contrast value of all N BGA balls can be generated by $$\delta = \frac{\sum_{i=1}^{N}\delta_i}{N}. \quad (6)$$

After obtaining the standard deviation $\sigma$ and the local contrast value $\delta$, the combined confidence measure of the BGA ball modeling is calculated using Equation 1 in step 309. The constant k is determined from the BGA ball modeling experiments, which is set to 1.0 for the current BGA ball modeling application.

Figure 5:
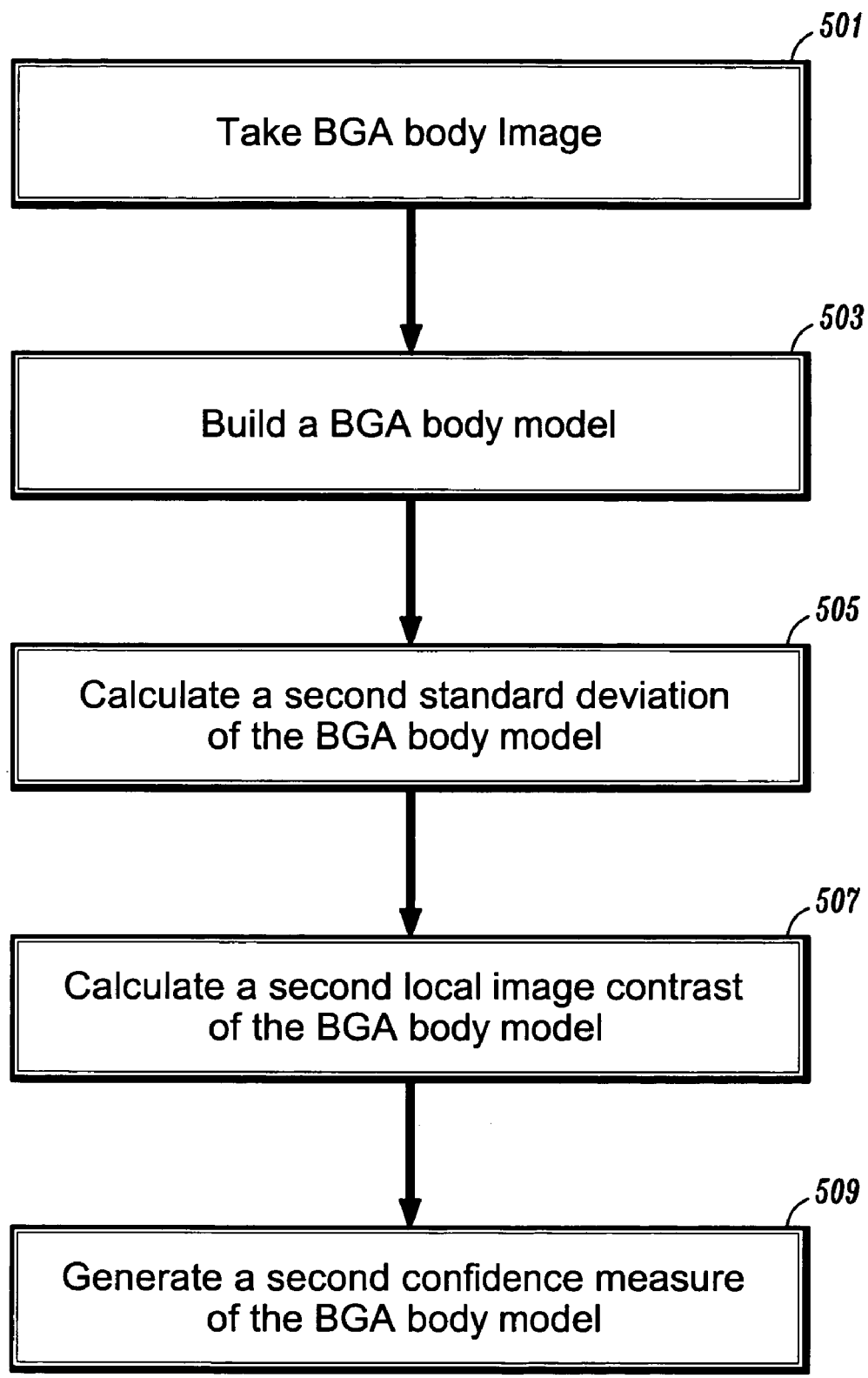
FIG. 5 illustrates a detailed process of generating a second confidence measure of a BGA body model according to an embodiment of the present invention.

FIG. 5 illustrates a detailed process of generating a second confidence measure of a BGA body according to an embodiment of the present invention. As described above, the BGA component consists of a set of BGA balls and a body that defines the boundary of the BGA component.

With a body image extracted through image processing and extraction techniques in step 501, generation of a ball gird array (BGA) body model is provided in step 503. For generation of the BGA body model, firstly, regions of interest (ROIs) are set for the BGA body to be modeled. Then, four body boundaries are detected to localize four corner coordinates. Based on orientations of four boundaries, a body orientation is determined after an orientation of each boundary is calculated by the projection of the edge of boundary. Then, four boundaries of the body are localized to obtain four corner coordinates for modeling the GBA body by calculating intersection positions of two adjacent boundary lines.

The confidence measure of a BGA body can be generated by the confidence measure for localizing boundary lines of the body. Based on the general confidence measure method discussed above with FIGS. 3 and 4, the confidence measure of BGA body modeling can also be calculated as a function of the standard deviation of the line modeling and the local image contrast around the boundary lines.

In step 505, a second standard deviation of the BGA body model having a plurality of boundary lines is calculated. As is shown above in the confidence measure determination for BGA balls, the confidence measure for the BGA body is also based on the following assumptions: (1) an BGA component image contains only one BGA component; (2) all four boundaries of one BGA component are assumed to be similar and visible; and (3) illumination condition is the same for all four boundary lines.

Under the above assumptions, if a BGA body model containing information about the location and orientation of the four boundary lines is correctly and accurately generated, then the sub-images containing each boundary extracted from the BGA component image should be similar except the orientation, and the standard deviation of these sub-images should be small. However, if a BGA model is not accurate in describing the location or the orientation of the four boundary lines, the sub-images containing the boundary lines will have varying image content that can lead to an increased standard deviation of these sub-images.

Figure 6:
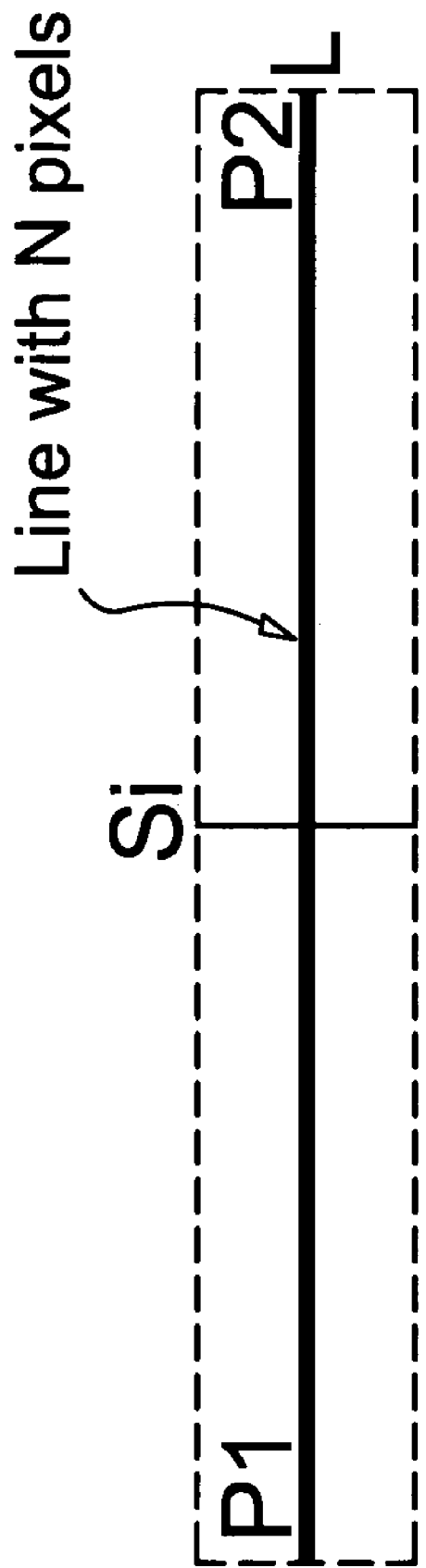
FIG. 6 shows a N×L line widow encompassing a boundary line of a BGA body model that includes a plurality of boundary lines.

FIG. 6 shows a N×L line widow encompassing one boundary line of a BGA body that includes a plurality of boundary lines. Let T represents a modeled boundary line that connects two end points of $P_1$ and $P_2$. The length of line T is N. From a BGA body image, a local window containing N by L pixels is selected which includes the modeled boundary line. N is the line length and L is a predefined size of the local window perpendicular to a direction of line N. If we define $S_i$ as a line segment at location i of Line T, which is perpendicular to the direction of line N, as shown in FIG. 3, N segments S can be obtained from the local window.

Similar to the ball window standard deviation calculation, mean value of these N segments of the BGA body boundary line can be determined from $$\overline{S} = \frac{\sum_{i=1}^{N}S_i}{N}, \quad (7)$$

and the standard deviation of line T is, therefore, can be calculated by $$\sigma_T = \frac{\sum_{j=1}^{L}\left(\sqrt{\frac{\sum_{i=1}^{N}(S_i-\overline{S})^2}{N-1}}\right)}{L}. \quad (8)$$

Here, let M be a total number of boundary lines of the BGA body. Then, the second standard deviation of the BGA body model is calculated as follows:

$$\sigma = \frac{\sum \sigma_T}{M}. \quad (9)$$

Next, a second local image contrast of the BGA body model is calculated by step 507 in FIG. 5. Similar to the local contract calculation of BGA balls, the local image contrast value of each segment is also calculated by performing a gradient operation. For i-th segment of the boundary line T, the local image contrast in the boundary region can be determined by $$\Delta_i = \max|A(k) - A(k-1)| \quad (10).$$

The contrast for the line T can then be obtained from $$\delta_T = \frac{\sum_{i=1}^{N} \Delta_i}{N}. \quad (11)$$

And the second local image contrast value of the BGA body can be calculated as $$\delta = \frac{\sum \delta_T}{M}, \quad (12)$$

where M is a total number of boundary lines of the BGA body. Typically, since the BGA body includes 4 boundary lines, M is 4.

Again using Equation (1), the second confidence value of BGA body modeling is obtained in step 509. The constant k is determined from the BGA body modeling experiments, the range of which is normally determined from 0 to 1.

Figure 7A:
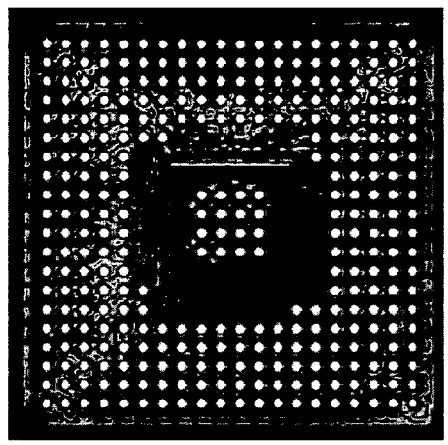
FIGS. 7, 8, and 9 show images containing BGA components "BGA 2I1," "BGA Blau," and "BGA 3I1," respectively, before and after modeling a BGA component.
Figure 7B:
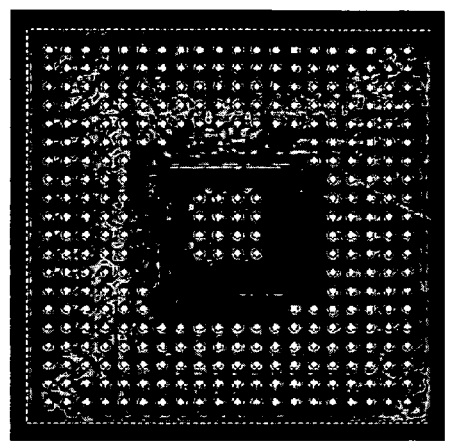

FIG. 7 shows images containing component "BGA 2I1," with FIG. 7(*a*) before and FIG. 7(*b*) after the modeling, respectively. The confidence values, as shown in Table 1, for BGA ball modeling and BGA body modeling can be calculated using the equations (1) through (12).

Figure 8A:
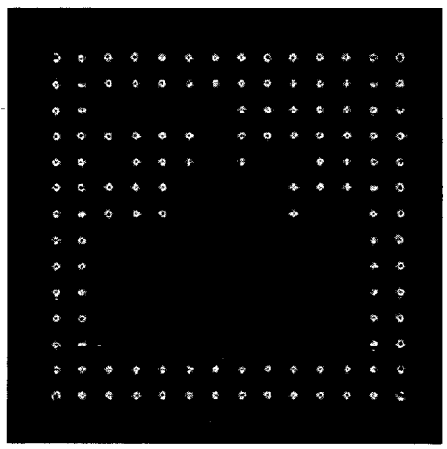
Figure 8B:
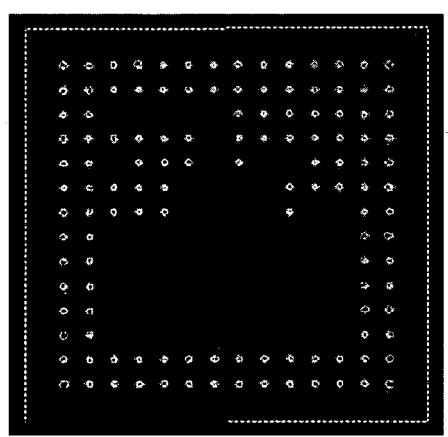
Figure 9A:
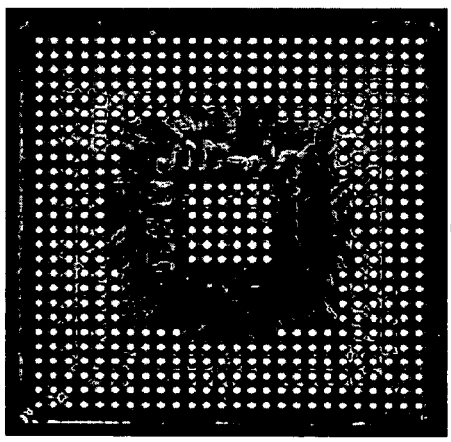
Figure 9B:
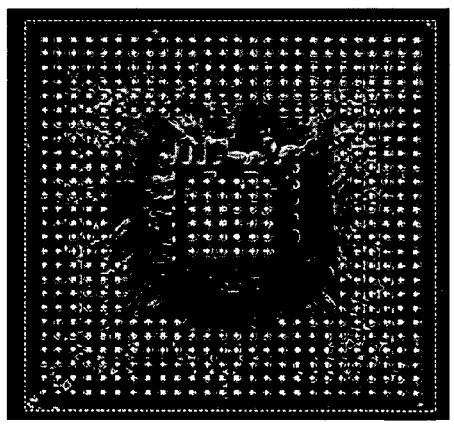

FIGS. 8 and 9 display images of "BGA Blau" and "BGA 3I1," with FIGS. 8(*a*) and 9(*a*) before, and FIGS. 8(*b*) and 9(*b*) after modeling, respectively. The confidence measure results are also shown in Table 1.

TABLE 1

The confidence values of BGA ball and body modeling for three different BGA components

| Conf. measures | BGA Type | | |
| --- | --- | --- | --- |
| | BGA 2I1 | BGA Blau | BGA 3I1 |
| σ of BGA ball | 4.6828 | 3.097 | 4.2145 |
| δ of BGA ball | 71.6142 | 20.4524 | 69.3008 |
| ρ of BGA ball | 0.9346 | 0.8486 | 0.9392 |
| σ of BGA body | 0.7717 | 0.2922 | 0.7043 |
| δ of BGA body | 76.8512 | 11.4605 | 53.2574 |
| ρ of BGA body | 0.8996 | 0.7451 | 0.8678 |

From table 1, it is noted that the standard deviation value σ of ball modeling for component BGA 2I1 is close to that of component BGA 3I1. Their local image contrast values δ are also close. Therefore, both components have approximately the same confidence value p. This is to be expected since the visual similarity of both BGA components is obvious, such as the illumination condition for the balls and bodies. In comparison, the standard deviation value σ of ball modeling for BGA Blau is only slightly lower than that of BGA 2I1 or BGA 3I1, while its local image contrast value δ for ball modeling is lower than that of BGA 2I1 or BGA 3I1. Therefore, the confidence measure of BGA Blau is lower than that of BGA 2I1 or BGA 3I1. This can also been seen clearly from FIGS. 7–9. The low local image contrast value of ball modeling for BGA Blau relates to a relatively poor illumination or difficult surface condition of BGA Blau, while the slightly lower standard deviation value σ of ball modeling for BGA Blau indicates that the ball modeling is comparatively well performed. Furthermore, the confidence measures of BGA body modeling are lower for all three testing components than those of BGA ball modeling. This indicates that the BGA body illumination and localization conditions are worse than those of BGA ball, which can easily be verified with the images shown in FIGS. 7–9. The lowest confidence measure is obtained from the body modeling for BGA Blau. The lowest confidence measure from Table 1 indicates the most unfavorable illumination and localization condition for modeling the body of BGA Blau, which can again be seen very clearly from FIG. 8, where the very low image contrast in the body boundary regions makes the body localization and modeling less reliable.

Figure 10:
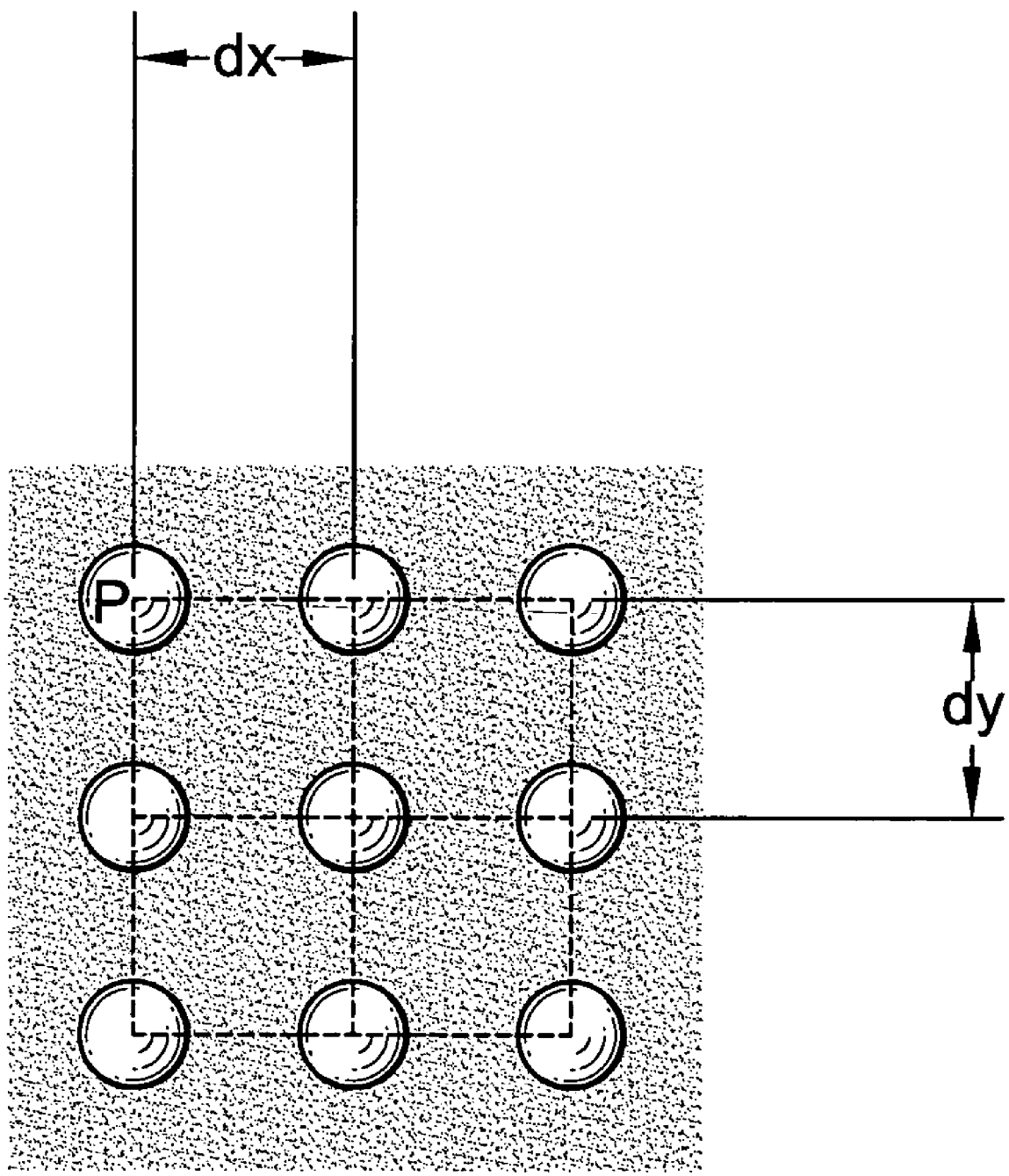
FIG. 10 shows a set of BGA balls of a BGA ball model having different parameters.
Figure 11A:
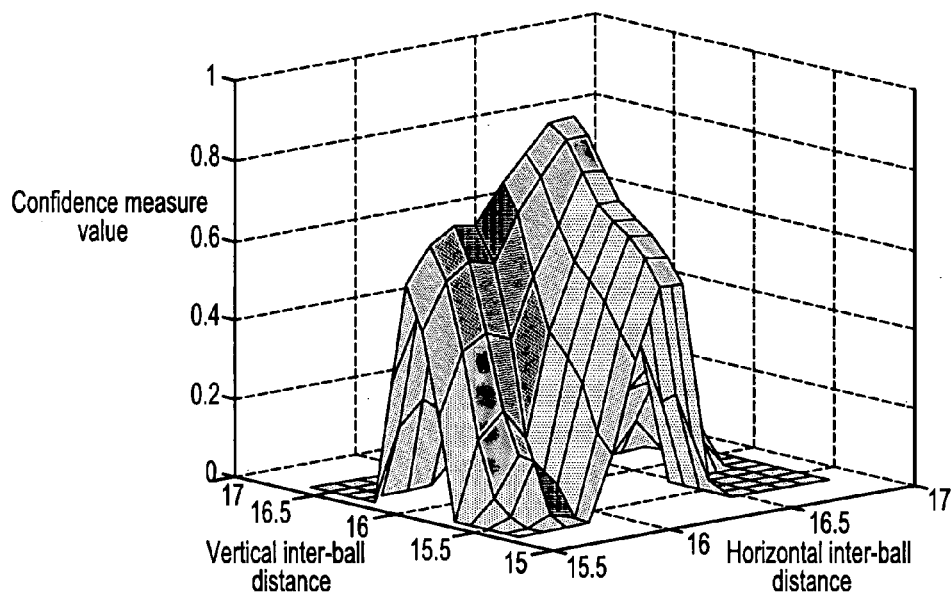
FIGS. 11(a) through 11(e) show confidence measure values and image examples based on inaccurate inter-ball distance in horizontal and vertical direction with low confidence measure.
Figure 11B:
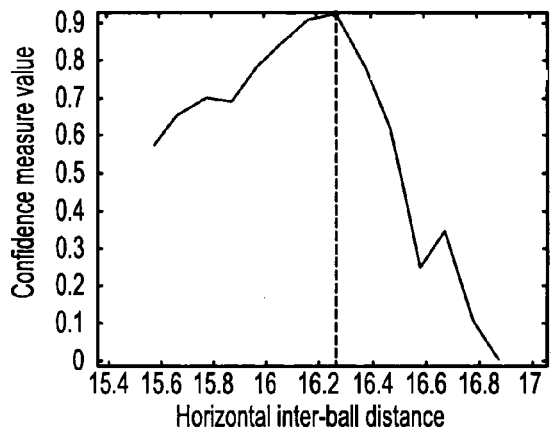
Figure 11C:
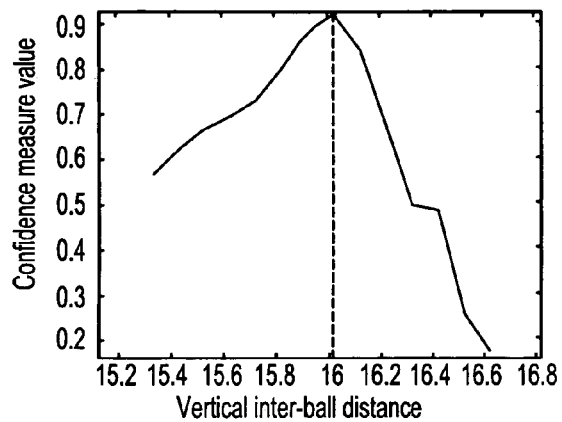
Figure 11D:
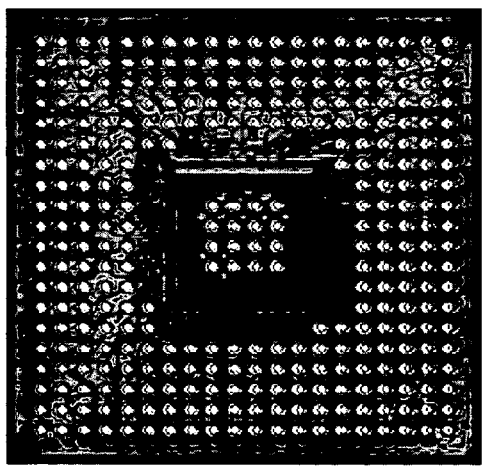
Figure 11E:
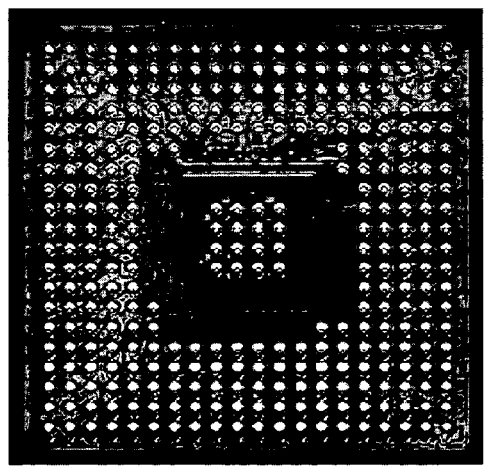

In the above experiments, it is proven that the proposed confidence measure is reliable when the model is accurately generated. Next, it is investigated what happens to the confidence measure when the BGA model is somehow inaccurately generated. A typical BGA model and its main parameters are shown in FIG. 10 and Table 2. BGA 2I1 is used as a test example for the following case.

TABLE 2

6 model parameters of a BGA model and the corresponding values for BGA 2I1

| Name | Description | Accurate model parameter value for BGA 2I1 as a test example |
| --- | --- | --- |
| Px | X coordinate of the top-left corner Ball | 166.2 |
| Py | Y coordinate of the top-left corner Ball | 86.4 |
| dx | Horizontal inter-ball distance | 16.2632 |
| dy | Vertical inter-ball distance | 16.0263 |
| r | Ball radius | 4.0542 |
| θ | BGA Ball grid orientation | 0° |

FIG. 11 shows confidence measures as a function of horizontal (FIG. 11(*b*)), vertical (FIG. 11(*c*)), and both (FIG. 11(*a*)) inter-ball distances. The confidence measure reaches its peak at the correct inter-ball distance as indicated in FIGS. 11(*b*) and 11(*c*). FIGS. 11(*d*) and 11(*e*) show two image examples of inaccurate inter-ball distance in horizontal and vertical direction with very low confidence measure wherein FIG. 11(*d*) is a BGA ball model with dx=16.5 and p=0.24, and FIG. 11(*e*) is a BGA ball model with dy=16.5 and p=0.25.

In the first experiment with incorrect or inaccurate model parameters, the confidence measure was computed as a function of the inter-ball distances in one and both directions, as shown in FIGS. 11(a) through 11(e). As expected, the confidence measure drops significantly when one of the model inter-ball distance or both are inaccurately extracted during the modeling process. This indicates that the proposed confidence measure provides a reasonable indication about the accuracy of the generated model. The confidence measure will drop significantly when the model inter-ball distance parameter is only offset by one pixel.

In the second experiment with incorrect or inaccurate model parameters, the confidence measure was computed as a function of the position of the top-left corner ball. In fact, this parameter determines the start position of the whole BGA ball grid, since all BGA ball are expected to be on a rectangular grid. The results are depicted in FIGS. 12(a) through 12(e).

FIGS. 12(a) through 12(c) shows confidence measure as the function of the x position of the left-top corner ball (FIG. 12(b)), the y position of the left-top corner ball (FIG. 12(c)), and both (FIG. 12(a)) x and y positions. The confidence measure reaches its peak at the correct x and y position of the top-left corner ball as indicated by the red dotted lines.

FIGS. 12(d) and 12(e) show two image examples of incorrect x or y position of the top-left corner ball with consequently low confidence measure wherein FIG. 12(d) is a BGA ball model with Px=168 and p=0.31, and FIG. 12(e) is a BGA ball model with Py=89 and p=0.48.

As expected, the confidence measure decreases significantly when the position of first top-left ball in the BGA model is inaccurately extracted during the modeling process. This verifies again that the proposed confidence measure provides a reasonable indication about the accuracy of the generated model relating to the start position of the BGA grid.

In the third experiment with incorrect or inaccurate model parameters, it is understood what results in when the BGA ball radius is inaccurately determined during the modeling process. Again, the confidence measure was computed as a function of BGA ball radius. The results are shown in FIGS. 13(a) and 13(b).

Figure 13A:
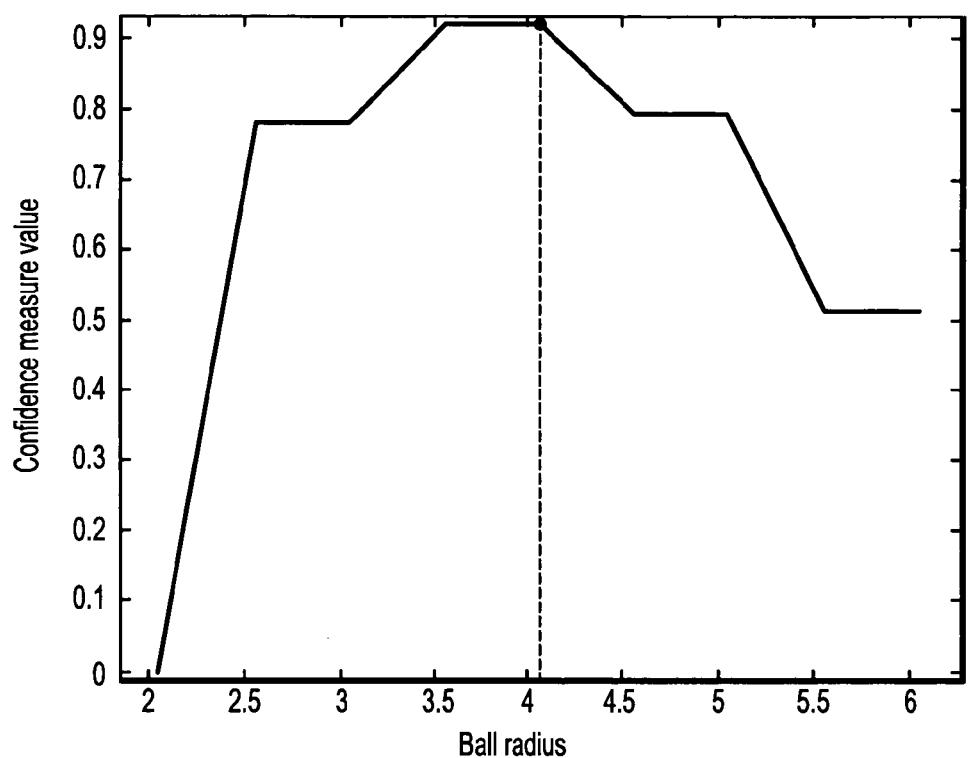
FIGS. 13(a) and 13(b) show confidence measure values and an image example based on incorrect radius with consequently low confidence measure.
Figure 13B:
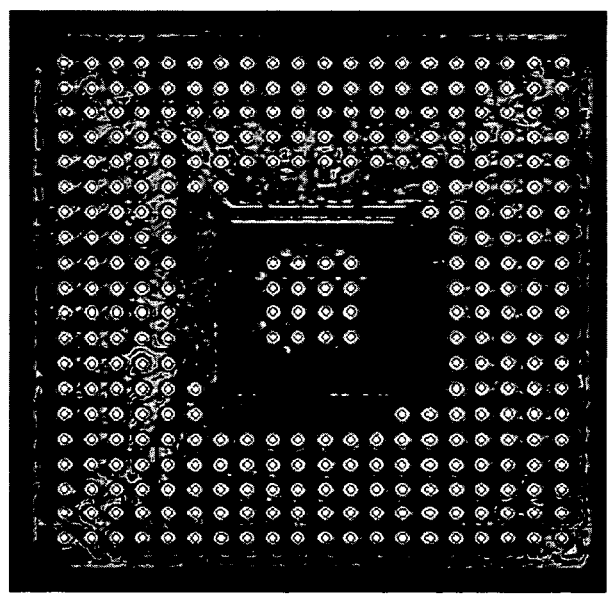

FIG. 13(a) shows confidence measure as a function of the ball radius. Here, the confidence measure in general decreases when the ball radius is inaccurately determined. FIG. 13(b) shows an example of a BGA model with an inaccurately determined radius of 3.0 (in this case, accurate model radius is 4.0542) and a relatively low confidence measure p of 0.77.

As expected, the confidence measure decreases when the radius of the BGA ball is inaccurately determined. However, as shown in FIG. 13(a), the confidence measure does not decrease if the ball radius is only slightly smaller (0.5 pixel) than the correct one. This indicates that the proposed confidence measure, although very general, may not be very sensitive in this particular case. In general, the BGA ball has a fuzzy, almost continues changing circle boundary from dark to bright. This transition is not very sharp. It is sometimes even difficult for a user to decide the correct ball boundary with sub-pixels accuracy. Therefore, this insensitivity of the confidence measure for slightly small radius reflects the fuzziness of the actual ball boundary. When the error in ball radius exceeds a certain threshold, the confidence measure does drop significantly, which represents a reasonable indication about the accuracy of the generated model relating to the radius of the BGA ball.

Figure 14A:
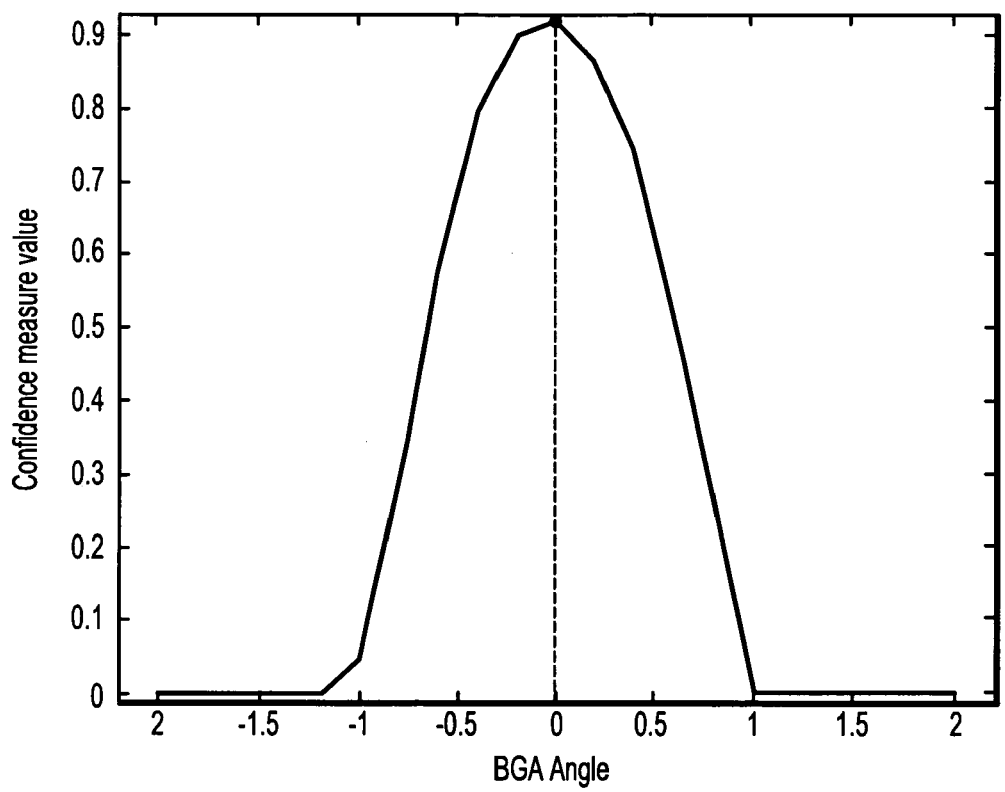
FIGS. 14(a) and 14(b) show confidence measure values and an image example based on orientation change of a BGA model.
Figure 14B:
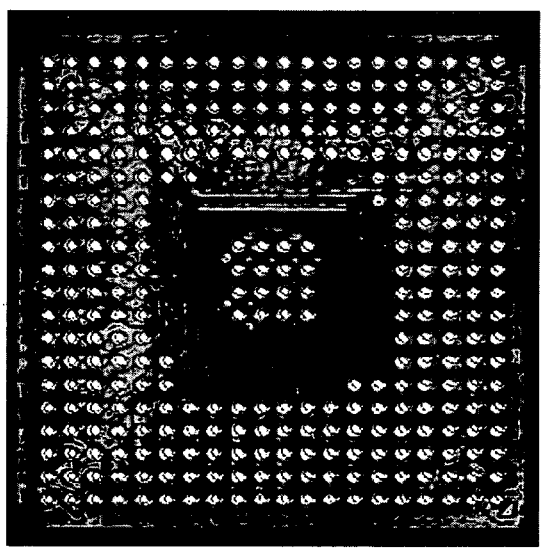

In the fourth experiment, the sensitivity of the proposed confidence measure is investigated as a function of the orientation of the generated BGA model, as shown in FIGS. 14(a) and 14(b).

FIG. 14(a) shows the confidence measure as a function of the orientation of the BGA model, and FIG. 14(b) shows an example of the BGA model with only 0.5 degree orientation change. When the confidence measure p is 0.6, this low confidence measure provides a good indication of the model accuracy. As expected, the confidence measure drops reasonably well when the orientation of the BGA model is inaccurately determined. The confidence measure drops to almost zero if the rotation angle has an error above one degree. This proves again that the proposed confidence measure is suitable for indicating the correctness of the BGA model orientation.

It is readily apparent to one skilled in the art that the methods of confidence measure disclosed above can be extended to other SMD component modeling applications since most SMD components contain only line and circular structures.

While the present invention has been described in detail with reference to the preferred embodiments, those skilled in the art will appreciate that various modifications and substitutions can be made thereto without departing from the spirit and scope of the present invention as set forth in the appended claims.

What is claimed is:

1. A method for obtaining confidence measure of a ball grid array (BGA) model having a plurality of balls in semiconductor surface mounted devices, the method comprising the steps of:

extracting BGA images from a surface mounted device having a BGA component;

building a BGA ball model and a BGA body model, the BGA ball model having geographic information of the BGA balls and the BGA body model having geographic information of the BGA body;

generating a first confidence measure of the BGA ball model wherein the first confidence measure includes a first standard deviation of the BGA ball model and a first local image contrast of each BGA ball; and generating a second confidence measure of the BGA body model wherein the second confidence measure includes a second standard deviation of the BGA body model and a second local image contrast of the BGA body.

2. The method according to claim 1, the step of generating the first confidence measure further comprising selecting a local ball window with n by n pixels, wherein a size of the local window is selected to be greater than or equal to a diameter of a ball such that the local window completely encompasses the ball.

3. The method according to claim 2, further comprising placing the local ball window symmetrically around the ball such that a window center corresponds to a ball center.

4. The method according to claim 1, wherein the first standard deviation σ is defined as follows:

$$\sigma = \frac{\sum_{j=1}^{L}\left(\sqrt{\frac{\sum_{i=1}^{N}(X_i - \overline{X})^2}{N-1}}\right)}{L},$$

where $X_i$ is an image vector of the ball window containing ith ball, $\overline{X}$ is a mean vector of N number of BGA ball windows, and L is a length of the image vector.

5. The method according to claim 4, wherein the mean vector $\overline{X}$ of N number of BGA ball windows is calculated as follows:

$$\overline{X} = \frac{\sum_{i=1}^{N} X_i}{N}.$$

6. The method according to claim 5, wherein the first local image contrast is calculated using a gradient operation based on a magnitude of an image gradient vector along a direction that is perpendicular to the tangent of the ball model.

7. The method according to claim 6, the step of generating the first confidence measure further comprising obtaining four local image contrast values of the BGA ball model, thereby calculating a local image contrast value $\delta_i$ of ball i as follows:

$$\delta_i = \frac{\Delta_{left} + \Delta_{right} + \Delta_{top} + \Delta_{bottom}}{4},$$

where $\Delta_{left}$, $\Delta_{right}$, $\Delta_{top}$, or $\Delta_{bottom}$ is a magnitude of an image gradient vector along a direction that is perpendicular to the tangent of the ball model at the left, the right, the top, or the bottom side of the ball model, respectively.

8. The method according to claim 7, the calculating step further comprising generating the first local image contrast $\delta$ of the BGA ball model having N number of BGA balls as follows:

$$\delta = \frac{\sum_{i=1}^{N} \delta_i}{N}.$$

9. The method according to claim 8, wherein the confidence measure for the BGA ball model is obtained by $$p = 1 - k\frac{\sigma}{\delta},$$

where p is the confidence measure, and k is a constant.

10. The method according to claim 1, the step of generating the second confidence measure of a BGA body model further comprising selecting a local window encompassing a boundary line of a plurality of body boundary lines that define the BGA body, the local window containing N by L pixels where N is a line length and L is a predefined size of the local window perpendicular to a line direction of N.

11. The method according to claim 10, the step of generating the second confidence measure further comprising dividing the local window into N segments $S_i$ to obtain mean value of these N segments of the boundary line, the mean value being defined as follows:

$$\overline{S} = \frac{\sum_{i=1}^{N} S_i}{N}.$$

12. The method according to claim 11, wherein standard deviation of the boundary line is calculated as follows:

$$\sigma_T = \frac{\sum_{j=1}^{L}\left(\sqrt{\sum_{i=1}^{N}(S_i - \overline{S})^2}\right)}{L}.$$

13. The method according to claim 12, wherein mean standard deviation of the BGA body model having M number of boundary lines is obtained by:

$$\sigma = \frac{\sum \sigma_T}{M}.$$

14. The method according to claim 1, the step of generating the second confidence measure of a BGA body model further comprising calculating the local image contrast of the BGA body model.

15. The method according to claim 14, the step of calculating the local image contrast is performed for each segment by a gradient operation.

16. The method according to claim 15, the step of calculating the local image contrast further comprising generating a line local image contrast for a modeled line T by:

$$\delta_T = \frac{\sum_{i=1}^{N} \Delta_i}{N},$$

where $\Delta_i$ is a magnitude of an image gradient vector for each segment.

17. The method according to claim 16, the step of calculating the local image contrast further comprising generating the second local image contrast value $\delta$ of the BGA body having M number of boundary lines as follows:

$$\delta = \frac{\sum \delta_T}{M}.$$

18. The method according to claim 17, wherein the confidence measure for BGA body model is obtained by $$p = 1 - k\frac{\sigma}{\delta},$$

where p is the confidence measure, and k is a constant.

19. A computer program storage device encoding computer program instructions executable by the computer to perform the method steps for obtaining confidence measure of a ball grid (BGA) model thereof in semiconductor surface mounted devices, the method steps comprising:

extracting BGA images from a real surface mounted device;

generating a BGA ball model and a BGA body model;

generating a first confidence measure of the BGA ball model wherein the first confidence measure includes a first standard deviation of the BGA ball model and a first local image contrast of each BGA ball; and generating a second confidence measure of the BGA body model wherein the second confidence measure includes a second standard deviation of the BGA body model and a second local image contrast of the BGA body.

20. The program storage device according to claim 19, the step of generating the BGA ball model and the BGA body model further comprising:

setting a plurality of regions of interest (ROIs) for all BGA balls to be modeled;

building a first grid model that includes coordinates and a diameter of the BGA balls in the plurality of ROIs;

setting a plurality of ROIs containing a BGA body to be modeled;

detecting four body boundaries to localize four corner coordinates; and determining a body orientation from orientations of four boundaries.

21. The program storage device according to claim 20, the step of generating the first confidence measure further comprising selecting a local ball window with n by n pixels, wherein a size of the local window is selected to be greater than or equal to a diameter of a ball such that the local window completely encompasses the ball.

22. The program storage device according to claim 21, further comprising placing the local ball window symmetrically around the ball of n by n pixels such that a window center corresponds to a ball center.

23. The program storage device according to claim 22, wherein the first standard deviation is defined as a function of an image vector of the ball window containing a specific ball, a mean vector of a number of BGA ball windows, and a length of the image vector.

24. The program storage device according to claim 23, wherein the first local image contrast is calculated using a gradient operation based on a magnitude of an image gradient vector along a direction that is perpendicular to the tangent of the ball model.

25. The program storage device according to claim 24, the step of generating the first confidence measure further comprising obtaining calculating a local image contrast value of each ball, thereby four local image contrast values of the BGA ball model.

26. The program storage device according to claim 25, wherein the confidence measure for the BGA ball model is obtained by a function of the first standard deviation and the first local image contrast value.

27. The program storage device according to claim 19, the step of generating the second confidence measure of a BGA body model further comprising selecting a local window encompassing a boundary line of a plurality of body boundary lines that define the BGA body.

28. The program storage device according to claim 27, the step of generating the second confidence measure further comprising dividing the local window into a number of segments to obtain mean value of the number of segments of the boundary line, thereby calculating the second standard deviation of the BGA body model.

29. The program storage device according to claim 28, the step of generating the second confidence measure of a BGA body model further comprising calculating the second local image contrast of the BGA body model as function of a magnitude of an image gradient vector for each segment of the boundary lines of the BGA body.

30. The program storage device according to claim 29, wherein the confidence measure for BGA body model is obtained by a function of the second standard deviation and the second local image contrast of the BGA body model.

* * * * *